United States Patent [19]
> Georgiev et al.

[11] Patent Number: 4,769,470

[45] Date of Patent: Sep. 6, 1988

[54] 5-(PHENYL OR PHENOXYALKYL)-3-(2-THIENYL)-3-(1H-IMIDAZOL-1-YLMETHYL)-2-METHYLISOXAZOLIDINES

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,702

[22] Filed: Oct. 2, 1987

[51] Int. Cl.$^4$ .................... A01N 43/52; C07D 233/60
[52] U.S. Cl. .................... 548/240; 548/336; 549/78
[58] Field of Search ........................................ 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa | 548/242 |
| 3,915,978 | 10/1975 | Kulsa | 548/240 |
| 3,987,179 | 10/1976 | Nadelson | 548/243 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS 171137   2/1986   European Pat. Off. ............ 548/215
54-76579   6/1979   Japan .

OTHER PUBLICATIONS

Boyce, C. B. (1977) Chem. Abstract 87:23258a.
Funaki, Y. (1980) Chem. Abstract 92:128915u.
Kelly, R. C. (1980) Chem. Abstract 93:114498u.
Haken, P. T. (1980) Chem. Abstract 93:132471i.
Sokolov, S. V. (1961) Chem. Abstract 55:7399.
Kano, H. (1965) Chem. Abstract 62:9139.
Kano, H. (1965) Chem. Abstract 63:8367a.
Takahi, Y. (1974) Chem. Abstract 81:22233c.

*Primary Examiner*—Donald G. Daus
*Assistant Examiner*—Mark W. Noel

[57] ABSTRACT

5-(Phenyl or phenoxymethyl)-3-(2-thienyl)-3-(1H-imidazol-1-ylmethyl)-2-methylisoxazolidines and related derivatives in which one or more hydrogens on the 5-phenyl or phenoxy rings are replaced by halogen, lower alkyl, lower alkoxy, nitro and combinations thereof are useful as antifungal agents.

9 Claims, No Drawings

5-(PHENYL OR PHENOXYALKYL)-3-(2-THIENYL)-3-(1H-IMIDAZOL-1-YLMETHYL)-2-METHYLISOXAZOLIDINES

BACKGROUND OF THE INVENTION

This invention pertains generally to substituted 2-methylisoxazolidines and more specifically to 5-(phenyl or phenoxymethyl)-3-(2-thienyl)-3-(1H-imidazol-1-ylmethyl)-2-methylisoxazolidines which are useful as antifungal agents.

BRIEF SUMMARY OF THE INVENTION

In accordance with this invention there are provided compounds of the formula:

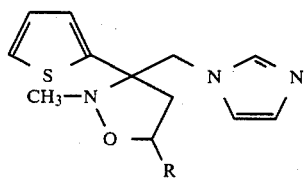

and the pharmaceutically acceptable acid addition salts thereof, in the form of their enantiomers or mixtures of their enantiomers including diastereoisomeric pairs of such enantiomers, wherein;

R is selected from phenyl, substituted phenyl, phenoxymethyl, substituted phenoxymethyl, phenylthiomethyl, ad (substituted phenyl)thiomethyl groups wherein the substituents on the substituted phenyl, phenoxymethyl and phenylthiomethyl groups are selected from halogen, nitro, lower alkyl, lower alkoxy and combinations thereof.

DETAILED DESCRIPTION OF THE INVENTION

The compounds of this invention are useful as antifungal agents. They have been shown to exert in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The thienyl compounds of Examples 1, 2, and 6 were found to have good to moderate activity against Trichophyton rubrum, Aspergillus fumigatus ad Candida albicans (minimum inhibitory concentration MIC, of <0.2 to 70 ug/ml).

Because of their antifungal activity, the compounds of the invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

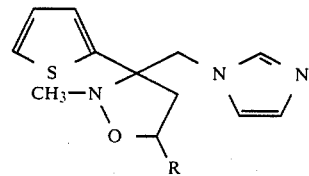

and the pharmaceutically acceptable acid addition salts thereof, in the form of their enantiomers or mixtures of their enantiomers including diastereoisomeric pairs of such enantiomers, wherein;

R represents phenyl, substituted phenyl, phenoxymethyl, substituted phenoxymethyl, phenylthiomethyl and (substituted phenyl)thiomethyl groups. The substituents on the substituted phenyl rings are selected from halogen, nitro, lower alkyl, lower alkoxy and combinations thereof. By halogen is meant chlorine, bromine, fluorine and iodine, with chlorine and fluorine being preferred. By lower alkyl is meant groups having one to four (1-4) carbons and by lower alkyl is meant groups having one to six (1-6 carbons which in either case can be a branched or unbranched chain.

The 5-(phenyl, phenoxymethyl or phenylthiomethyl)-3-(2-thienyl)-3-(1H-imidazol-1-ylmethyl)-2-methylisoxazolidine derivatives are obtained as mixtures of cis- and trans-diastereomers due to the presence of two asymmetric carbon atom in the isoxazolidine ring. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The said eluents may be used alone or in combinations, such as the ones comprised of 95-99% halogenated hydrocarbon and 1-5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis- and trans-diastereomers are resolvable into their optical enantiomers with (+)- and (−)-optical rotations by standard techniques such as fractional recrystallization of the diastereomeric salts with optically active organic acids such as (+)- and (−)-tartaric acid, (+)- and (−)-dibenzoyltartaric acid and the like.

As illustrated in the following diagram, the thienyl compounds of this invention can be prepared by an initial bromination of 2-acetylthiophene 1, and reacting the resulting bromo derivative 2 with imidazole to produce the 1-(2-thienyl)-2-(1H-imidazol-1-yl)ethanone 3. Reaction of compound 3 with N-methylhyroxylamine hydrochloride provides the 1-(2-thienyl)-2-(1H-imidazol-1-yl)-N-methylethanimine N-oxide 4 which is included in the subject matter of our co-pending application Ser. No. 900,856 filed Aug. 27, 1986 entitled "α-Substituted Ketonitrone Derivatives" whose disclosure is incorporated herein by reference. The nitrone compound 4 is then treated with styrene or an appropriate styrene (or allyl phenyl ether or alkyl phenyl thioether) derivative 5 to give a diastereomeric mixture of the desired cis- and trans-5-(phenyl, phenoxymethyl or phenylthiomethyl)-3-(2-thienyl)-3-(1H-imidazol-1-ylmethyl)-2-methylisoxazolidine 6.

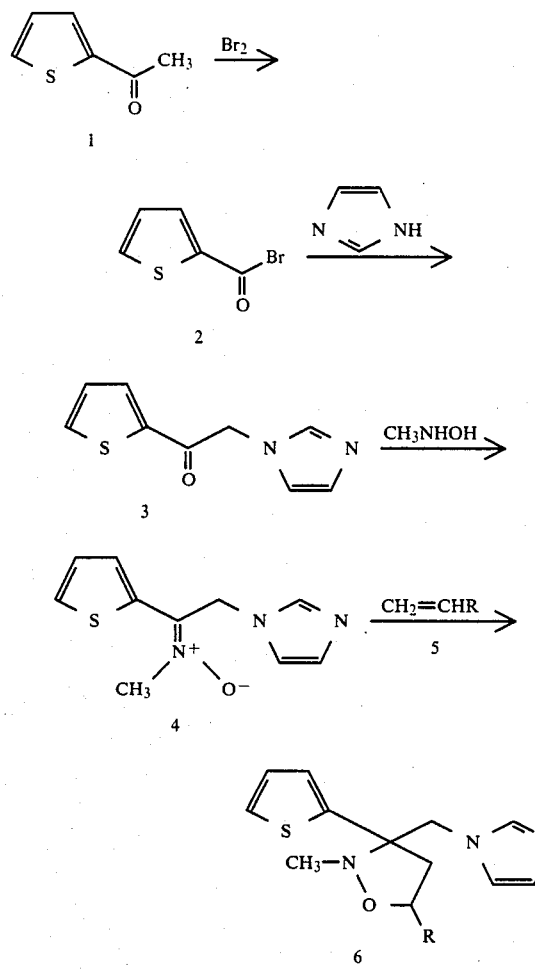

The compounds of this invention are basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of this invention is further illustrated by the following syntheses of intermediates and in the Examples.

Preparation of
2-(1H-Imidazol-1-yl)-1-(2-thienyl)ethanone (3)

Bromine (19.0 ml, 0.371 mol) is added dropwise over 40 minutes to an ice-cold solution of 40.75 g (0.323 mol) of 2-acetylthiophene in 200 ml of ether, under a nitrogen atmosphere. After stirring for 90 min, the reaction is quenched with 100 ml of saturated aqueous ammonium chloride. The layers are separated and the organic layer is washed with 100 ml of water, dried over anhydrous magnesium sulfate and concentrated in vacuo to give a yellow oil (compound 2), which is dissolved in 100 ml of ether and added over 1 hr to an ice-cold solution of 89.75 g (1.32 mol) of imidazole in 150 ml of methanol, under a nitrogen atmosphere. The reaction is stirred for 22 hrs at ambient temperature, diluted with 1 liter of water and extracted with chloroform (4×300 ml). The combined organic layer is dried over anhydrous magnesium sulfate, concentrated in vacuo and flash-chromatographed on neutral silica gel, using a 99:1 by volume mixture of chloroform and methanol as eluent, to give 36.10 g (58%) of compound 3, melting point 87°–89° C. (ethyl acetate). Anal. Calcd. for $C_9H_8N_2OS$: C, 56.23; H, 4.19; N, 14.57; S, 16.68. Found: C, 56.03; H, 4.28; N, 14.48; S, 16.39.

Preparation of
2-(1H-Imidazol-1-yl)-N-methyl-1-(2-thienyl)ethanimine N-oxide (4)

Under a nitrogen, a mixture of 22.00 g (0.114 mol) of 2-(1H-imidazol-1-yl)-1-(2-thienyl)ethanone (3), 11.49 g (0.138 mol) of N-methylhydroxylamine hydrochloride, and 22.55 g (0.275 mol) of sodium acetate in 250 ml of ethanol is heated to 50° C. and stirred for 4 days. The reaction mixture is filtered while hot and the filtrate concentrated in vacuo. Crystallization from ethanol gives 22.62 g (89%) of compound 4, melting point 162°–164° C. Anal. Calcd. for $C_{10}H_{11}N_3OS$: C, 54.28; H, 5.01; N, 18.99. Found: C, 54.16; H, 5.06; N, 18.86.

EXAMPLE 1

3-(1H-Imidazol-1-ylmethyl)-2-methyl-5-phenyl-3-(2-thienyl)isoxazolidine (6, R=C₆H₅)

A suspension of 4.04 g (0.018 mol) of 2-(1H-imidazol-1-yl)-N-methyl-1-(2-thienyl)ethanimine N-oxide (4) and 3.10 ml (1.50 equiv) of styrene in 100 ml of toluene is refluxed for 72 hrs under a nitrogen atmosphere. The reaction mixture is cooled to ambient temperature and filtered. The filtrate, containing the cis- and trans-diastereomeric mixture of compound 6 (R=C₆H₅), is concentrated in vacuo and flash-chromatographed on neutral silica gel using a 98:2 mixture of chloroform and methanol as eluent.

Isomer A (2.68 g, 45%) has a melting point of 89°–92° C. (ethyl acetate). Anal. Calcd. for $C_{18}H_{19}N_3OS$: C, 66.44; H, 5.88; N, 12.91. Found: C, 66.34; H, 5.91; N, 12.92.

EXAMPLE 2

5-(4-Chlorophenyl)-3-(1H-imidazol-1-ylmethyl)-2-methyl-2-methyl-3-(2-thienyl)isoxazolidine (6, R=C₆H₄Cl-4)

Compound 6 (R=C₆H₄Cl-4) is prepared by a method similar to that described in Example 1 by reacting 2-(1H-imidazol-1-yl)-N-methyl-1-(2-thienyl)ethanimine N-oxide 4 with 4-chlorostyrene. The resulting cis- and trans-diastereomeric mixture of compound 6 (R=C₆H₄Cl-4) is flash-chromatographed on neutral silica gel using ethyl acetate as eluent. Isomer A has a melting point of 125°–127° C. (ethyl acetate). Anal. Calcd. for $C_{18}H_{18}ClN_3OS$: C, 60.08; H, 5.04; Cl, 9.85; N, 11.68. Found: C, 60.12; H, 5.05; Cl, 10.10; N, 11.70.

Isomer B has a melting point of 149°–152° C. (ethyl acetate). Anal Calcd. for $C_{18}H_{18}ClN_3OS$: C, 60.08; H, 5.04; Cl, 9.85; N, 11.68. Found: C, 60.17; H, 5.16; Cl, 10.13; N, 11.69.

EXAMPLE 3

3-(1H-Imidazol-1-ylmethyl)-2-methyl-5-(3-nitrophenyl)-3-(2-thienyl)isoxazolidine (6, R=C₆H₄NO₂-3)

Compound 6 (R=C₆H₄NO₂-3) was prepared by a method similar to that described in Example 1 by reacting 2-(1H-imidazol-1-yl)-N-methyl-1-(2-thienyl)ethanimine N-oxide (4) with 3-nitrostyrene. The resulting cis- and trans-diastereomeric mixture of compound 6, ($R = C_6H_4NO_2$-3) is flash-chromatographed on neutral silica gel using a 98:2 mixture by volume of chloroform and methanol as eluent. Isomer A has a melting point of 154.5°–156° C. (ethanol). Anal. Calcd. for $C_{18}H_{18}N_4O_3S$: C, 58.36; H, 4.90; N, 15.12. Found: C, 57.50; H, 4.87; N, 14.92.

EXAMPLE 4

3-(1H-Imidazol-1-ylmethyl)-2-methyl-5-(phenoxymethyl)-3-(2-thienyl)isoxazolidine (6, $R = CH_2OC_6H_5$)

Compound 6 ($R = CH_2OC_6H_5$) was prepared by a method similar to that described in Example 1 by reacting 2-(1H-imidazol-1-yl)-N-methyl-1-(2-thienyl)ethanimine N-oxide (4) with allyl phenyl ether. The resulting cis- and trans-diastereomeric mixture of compound 6 ($R = CH_2OC_6H_5$) is flash-chromatographed on neutral silica gel using a 98:2 mixture by volume of chloroform and methanol as eluent.

Isomer A has a melting point of 107°–109° C. (ethyl acetate). Anal. Calcd. for $C_{19}H_{21}N_3O_2S$: C, 64.20; H, 5.95; N, 11.82. Found: C, 64.30; H, 6.09; N, 11.84.

Isomer B has a melting point of 144°–146° C. (ethyl acetate). Anal. Calcd. for $C_{19}H_{21}N_3O_2S$: C, 64.20; H, 5.95; N, 11.82. Found: C, 64.31; H, 6.18; N, 11.79.

EXAMPLE 5

5-[(4-Chlorophenoxy)methyl]-3-(1H-imidazol-1-ylmethyl)-2-methyl-3-(2-thienyl)isoxazolidine (6, $R = CH_2OC_6H_4Cl$-4)

Compound 6 ($R = CH_2OC_6H_4Cl$-4) is prepared by a method similar to that described in Example 1 by reacting 2-(1H-imidazol-1-yl)-N-methyl-1-(2-thienyl)ethanimine N-oxide (2) with allyl 4-chlorophenyl ether. The resulting cis- and trans-diastereomeric mixture of compound 6 ($R = CH_2OC_6H_4Cl$-4) is flash-chromatographed on neutral silica gel using ethyl acetate as eluent.

Isomer A has a melting point of 118°–120° C. (ethyl acetate). Anal. Calcd. for $C_{19}H_{20}ClN_3O_2S$: C, 58.53; H, 5.17; N, 10.78; S, 8.22. Found: C, 58.69; H, 5.23; N, 10.76; S, 8.50.

Isomer B has a melting point of 95°–99° C. (ethyl acetate). Anal. Calcd. for $C_{19}H_{20}ClN_3O_2S$: C, 58.53; H, 5.17; Cl, 9.09; N, 10.78; S, 8.22. Found: C, 58.50; H, 5.23; Cl, 9.29; N, 10.68; S, 8.18.

EXAMPLE 6

3-(1H-Imidazol-1-ylmethyl)-2-methyl-5-[[(4-methylphenyl)thio]methyl]-3-(2-thienyl)isoxazolidine (6, $R = CH_2SC_6H_4$—$CH_3$-4)

Compound 6 ($R = CH_2SC_6H_4CH_3$-4) is prepared by a method similar to that described in Example 1 by reacting 2-(1H-imidazol-1-yl)-N-methyl-1-(2-thienyl)ethanimine N-oxide (4) with allyl 4-methylphenyl sulfide. The resulting cis- and trans-diastereomeric mixture of compound 6 ($R = CH_2SC_6H_4CH_3$-4) is flash-chromatographed on neutral silica gel using ethyl acetate as eluent.

Isomer A has a melting point of 205°–210° C. (decomp.) (ethanol) as its monohydrochloride salt. Anal. Calcd. for $C_{20}H_{24}ClN_3OS_2$: C, 56.92; H, 5.73; Cl, 8.40; N, 9.96 S, 15.20. Found: C, 56.88; H, 5.92; Cl, 8.66; N, 9.97; S, 15.30.

Isomer B has a melting point of 159°–161° C. (ethanol-ether, 1:1 by volume) as its monohydrochloride salt. Anal. Calcd. for $C_{20}H_{24}ClN_3OS_2$: C, 56.92; H, 5.73; Cl, 8.40; N, 9.96; S, 15.20. Found: C, 56.78; H, 5.82; l N, 9.92.

EXAMPLE 7

5-[[4-Chlorophenyl)thio]methyl]-3-(1H-imidazol-1-ylmethyl)-2-methyl-3-(2-thienyl)isoxazolidine (6, $R = CH_2SC_6$—$H_4Cl$-4)

Compound 6 ($R = CH_2SC_6H_4Cl$-4) is prepared by a method similar to that described in Example 1 by reacting 2-(1H-imidazol-1-yl)-N-methyl-1-(2-thienyl)ethanimine N-oxide (4) with allyl 4-chlorophenyl sulfide. The resulting cis- and trans-diastereomeric mixture of compound 6 ($R = CH_2SC_6H_4Cl$-4) is flash-chromatographed on neutral silica gel using a 99:1 mixture by volume of ethyl acetate and methanol as eluent.

Isomer A has a melting point of 101°–104° C. (ethyl acetate). Anal. Calcd. for $C_{19}H_{20}ClN_3OS_2$: C, 56.21; H, 4.97; Cl, 8.73; N, 10.35; S, 15.79. Found: C, 56.30; H, 5.02; Cl, 8.98; N, 10.37; S, 15.47.

Isomer B has a melting point of 163°–173° C. (isopropanol) as its monhydrochloride salt.

EXAMPLE 8

3-(1H-Imidazol-1-ylmethyl)-5-[(4-methoxyphenoxy)methyl]-2-methyl-3-(2-thienyl)isoxazolidine (6, $R = CH_2OC_4OCH_3$-4)

Compound 6 ($R = CH_2OC_6H_4OCH_3$-4) can be prepared by a method similar to that described in Example 1 by reacting 2-(1H-imidazol-1-yl)-N-methyl-1-(2-thienyl)ethanimine N-oxide (4) with allyl 4-methoxyphenyl ether.

The compounds of the invention where R is lower alkyl phenyl can be prepared according to the method of Example 1 by substituting for styrene,
4-methylstyrene, bp 170°–175° C.,
and 3-methylstyrene, bp 170°–171° C.

The compound of the invention where R is lower alkylphenoxymethyl can be prepared according to the method of Example 5 by substituting for allyl 4-chlorophenyl ether, allyl 4-methylphenyl ether, bp 97°–98° C.

Salts of the compounds of the invention can be prepared as known in the art, for example, by dissolving the compound in a 10:1 by volume mixture of ethanol and aqueous acid such as HCl or $HNO_3$, evaporating the solvent, and then recrystallizing the crude salt, for example, from ethanol-ether, methanol-ether, 1:3 by volume or ethanol.

We claim:
1. A compound of the formula:

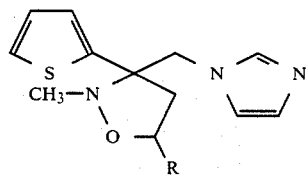

and the pharmaceutically acceptable acid addition salts thereof, in the form of their enantiomers or mixtures of their enantiomers including diastereoisomeric pairs of such enantiomers,
wherein;
R is selected from phenyl, substituted phenyl and phenoxymethyl, substituted phenoxymethyl, phenylthiomethyl, and (substituted phenyl)thiomethyl groups wherein the substituents on the substituted phenyl, phenylmethoxy and phenylthiomethyl groups are selected from one to three of halogen, nitro, lower alkyl, lower alkoxy and combinations thereof.

2. The compound of claim 1 wherein the compound is 3-(1H-imidazol-1-ylmethyl)-2-methyl-5-phenyl-3-(2-thienyl)isoxazolidine.

3. The compound of claim 1 wherein the compound is 5-(4-chlorophenyl)-3-(1H-imidazol-1-ylmethyl)-2-methyl-3-(2-thienyl)isoxazolidine.

4. The compound of claim 1 wherein the compound is 3-(1H-imidazol-1-ylmethyl)-2-methyl-5-(3-nitrophenyl)-3-(2-thienyl)isoxazolidine.

5. The compound of claim 1 wherein the compound is 3-(1H-imidazol-1-ylmethyl)-2-methyl-5-(phenoxymethyl)-3-(2-thienyl)isoxazolidine.

6. The compound of claim 1 wherein the compound is 5-[(4-chlorophenoxy)methyl]-3-(1H-imidazol-1-ylmethyl)-2-methyl-3-(2-thienyl)isoxazolidine.

7. The compound of claim 1 wherein the compound is 3-(1H-imidazol-1-ylmethyl)-2-methyl-5-[[(4-methylphenyl)thio]methyl]-3-(2-thienyl)isoxazolidine.

8. The compound of claim 1 wherein the compound is 5-[[(4-chlorophenyl)thio]methyl]-3-(1H-imidazol-1-ylmethyl)-2-methyl-3-(2-thienyl)isoxazolidine.

9. The compound of claim 1 wherein the compound is 3-(1H-imidazol-1-ylmethyl)-5-[(4-methoxyphenoxy)methyl]-2-methyl-3-(2-thienyl)isoxazolidine.

* * * * *